US00PP37461P2

(12) United States Plant Patent
Kaluzinski

(10) Patent No.: US PP37,461 P2
(45) Date of Patent: Jun. 9, 2026

(54) ***JUNIPERUS* PLANT NAMED 'KA5'**

(50) Latin Name: *Juniperus conferta*
Varietal Denomination: KA5

(71) Applicant: Michal Kaluzinski, Szadek (PL)

(72) Inventor: Michal Kaluzinski, Szadek (PL)

( * ) Notice: Subject to any disclaimer, the term of this patent is extended or adjusted under 35 U.S.C. 154(b) by 0 days.

(21) Appl. No.: 19/338,676

(22) Filed: Sep. 24, 2025

(51) Int. Cl.
*A01H 5/00* (2018.01)
*A01H 7/00* (2006.01)

(52) U.S. Cl.
USPC ..... Plt./214
CPC ..... *A01H 7/00* (2013.01)

(58) Field of Classification Search
USPC ..... Plt./214
CPC ..... A01H 7/00; A01H 5/00
See application file for complete search history.

*Primary Examiner* — Kent L Bell
(74) *Attorney, Agent, or Firm* — Penny J. Aguirre

(57) ABSTRACT

A new cultivar of *Juniperus conferta* plant named 'KA5' that is characterized by its dense and compact plant habit, its light yellow young shoots and mature green leaves, and its moderate growth rate.

2 Drawing Sheets

Botanical classification: *Juniperus conferta.*
Varietal denomination: 'KA5'.

BACKGROUND OF THE INVENTION

The present invention relates to a new and distinct cultivar of *Juniperus* and will be referred to hereafter by its cultivar name, 'KA5'. 'KAS' is a new cultivar of juniper, an evergreen shrub grown for use as an ornamental landscape plant.

The new cultivar was discovered by the Inventor in May of 2020 as a naturally occurring branch mutation of *Juniperus conferta* 'Schlager' (not patented) growing in a container in Szadek, Poland.

Asexual propagation of the new cultivar was first accomplished under the direction of the Inventor by stem cuttings in September of 2020 in Szadek, Poland. Propagation by tissue culture and division has determined the characteristics to be stable and reproduced true to type in successive generations.

SUMMARY OF THE INVENTION

The following traits have been repeatedly observed and represent the characteristics of the new cultivar. These attributes in combination distinguish 'KA5' as a unique cultivar of *Juniperus.*

1. 'KA5' exhibits a dense and compact plant habit.
2. 'KAS' exhibits light yellow young shoots and mature green leaves.
3. 'KA5' exhibits a moderate growth rate.

The parent plant of 'KA5' differs from 'KA5' in having a more vigorous plant habit and blue-green young shoots. 'KA5' can be compared to *Juniperus* cultivars 'Allgold' (not patented) and 'JAP08' (U.S. Plant Pat. No. 21,433). 'Allgold' and 'JAP08' are both similar to 'KA5' in having a flattened globular plant shape and a moderately vigorous growth habit. 'Allgold' differs in having foliage that is golden yellow in color and changes to orange-yellow in winter. 'JAP08' differs from 'KA5' in having young and mature foliage that is variegated with yellow patches throughout the plant.

BRIEF DESCRIPTION OF THE DRAWINGS

The plant and plant parts depicted in the accompanied photographs illustrate the characteristics of 'KA5'. The photographs were taken of an 18 month-old plant as grown outdoors in a 17-cm container in Meijel, The Netherlands.

The photograph in FIG. 1 provides an overall side view of the plant habit of 'KA5'.

Figure 1:
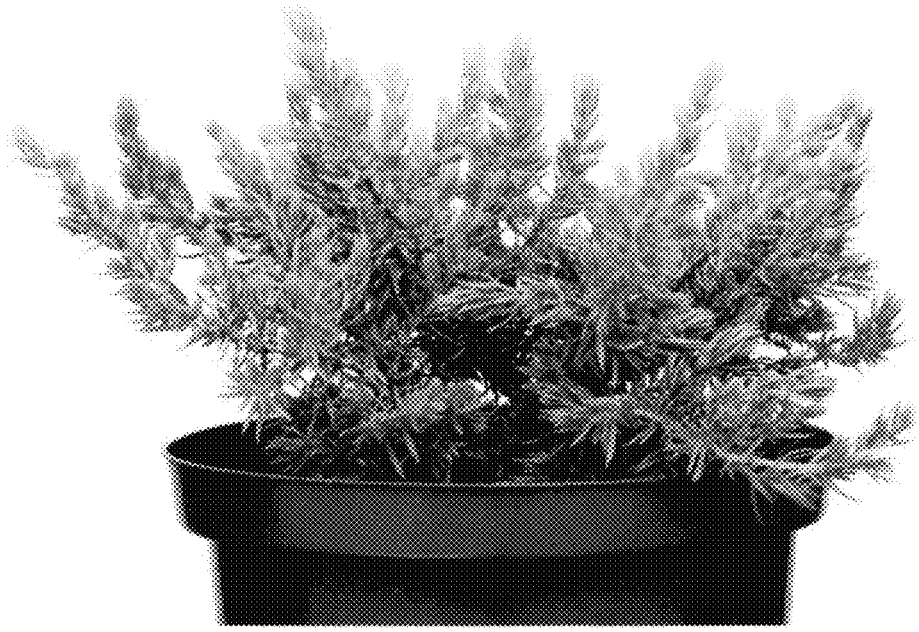
Figure 2:
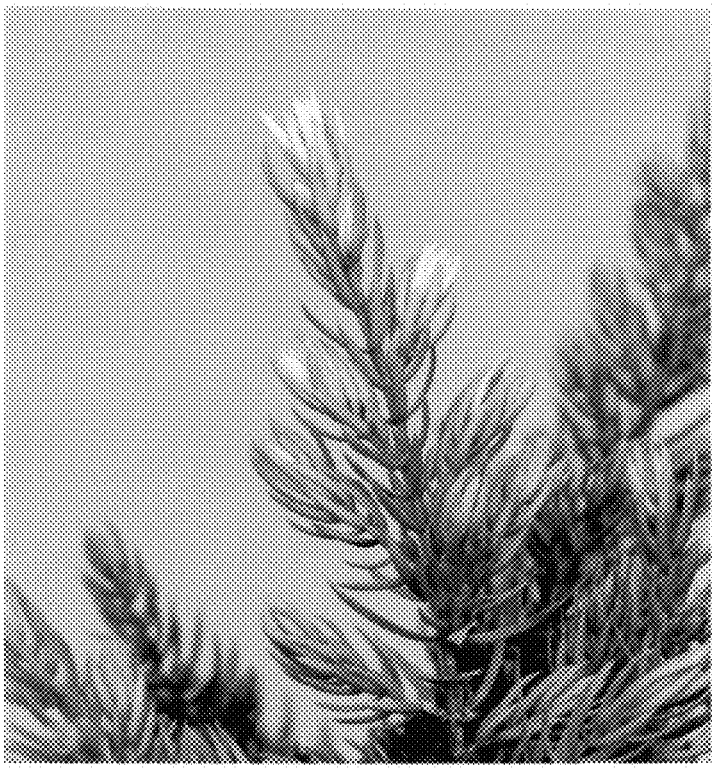

The photograph in FIG. 2 provides a close-up view of the young foliage of 'KA5'.

Figure 3:
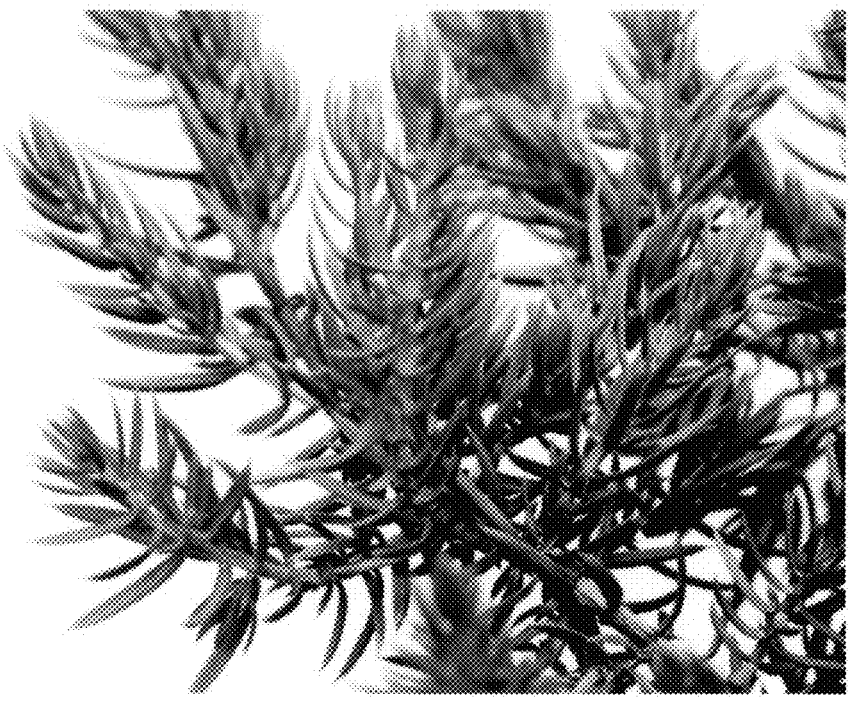

The photograph in FIG. 3 provides a close-up view of the mature foliage of 'KA5'.

The colors in the photographs are as close as possible with the photographic and printing technology utilized. The color values cited in the detailed botanical description accurately describe the colors of the new *Juniperus.*

DETAILED BOTANICAL DESCRIPTION

The following is a detailed description of the new cultivar as taken from an 18 month-old plant as grown outdoors in 17-cm containers in Meijel, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Plant type.*—Evergreen shrub.

*Plant habit.*—Flattened globular in shape, dense, and compact.

*Height and spread.*—An average of 14.2 cm in height and 15.4 cm in width as an 18-month-old plant grown in a container, reaches an average of 40 cm in height and 70 cm in width as grown in the landscape.

*Cold hardiness*.—At least to U.S.D.A. Zone 6.

*Diseases and pests*.—No resistance and susceptibility to diseases or pests have been observed.

*Root description*.—Fibrous, moderately branched, moderately thick, primarily 199A in color.

*Propagation*.—Stem cuttings.

*Root development*.—Roots initiate in 3 to 4 months, a rooted liner is produced in 8 months from a rooted cutting.

*Growth rate*.—Moderate.

Branch description:

*Branch shape*.—Rounded, young shoots quadrangular.

*Branch size*.—Average of 10.2 cm in length and 1.5 mm in diameter.

*Branch surface*.—Matte and glabrous.

*Branching*.—Main; 1, lateral; 18 per main branch.

*Branch aspect*.—Held at an average angle of 60° (varying between 30° and 90°) to main branch.

*Internode length*.—Average of 7 mm.

*Branch color*.—Young; 151A, mature; a blend of 172B and 172C, mature bark; N199A and N199B.

*Branch strength*.—Strong.

Foliage description:

*Leaf arrangement*.—Opposite in whorls of 3.

*Leaf attachment*.—Sessile.

*Leaf shape*.—Lanceolate, scale-like.

*Leaf division*.—Simple.

*Leaf base*.—Decurrent.

*Leaf apex*.—Apiculate, slightly sharp to touch.

*Leaf venation*.—Not distinguishable.

*Leaf margins*.—Entire.

*Leaf fragrance*.—When crushed, the foliage produces a strong pleasant smell.

*Leaf surface*.—Both surfaces glabrous and smooth, upper surface matte, lower surface slightly glossy.

*Leaf texture*.—Fine.

*Leaf color*.—Young upper surface; a blend of 150D and 1D, young lower surface; 6D, mature upper surface; 139D, margins 143C.

*Leaf size*.—Average of 1.2 cm in length and 1.5 mm in diameter.

*Leaf quantity*.—180 scale-like leaves per lateral branch.

Cone description: Cones have not observed on the new cultivar to date.

It is claimed:

1. A new and distinct cultivar of *Juniperus* plant named 'KA5' as herein illustrated and described.

* * * * *